(12) United States Patent
Rochat et al.

(10) Patent No.: US 8,562,971 B2
(45) Date of Patent: Oct. 22, 2013

(54) REDUCTION OF RISK DIARRHOEA

(75) Inventors: Florence Rochat, Montreux (CH); Karl-Josef Huber-Haag, Pully (CH); Marie-Claire Fichot, Blonay (CH)

(73) Assignee: Nestec S.A., Vevey (CH)

( * ) Notice: Subject to any disclaimer, the term of this patent is extended or adjusted under 35 U.S.C. 154(b) by 867 days.

(21) Appl. No.: 12/532,070

(22) PCT Filed: Feb. 20, 2008

(86) PCT No.: PCT/EP2008/052029
§ 371 (c)(1),
(2), (4) Date: Dec. 22, 2009

(87) PCT Pub. No.: WO2008/116708
PCT Pub. Date: Oct. 2, 2008

(65) Prior Publication Data
US 2010/0129335 A1    May 27, 2010

(30) Foreign Application Priority Data

Mar. 28, 2007 (EP) .................... 07105078

(51) Int. Cl.
*A01N 63/00* (2006.01)
*C12N 1/12* (2006.01)
*C12N 1/20* (2006.01)

(52) U.S. Cl.
USPC ... 424/93.3; 424/93.4; 424/93.45; 435/252.1; 435/252.4; 435/252.9; 435/853

(58) Field of Classification Search
None
See application file for complete search history.

(56) References Cited

U.S. PATENT DOCUMENTS

2007/0020249 A1    1/2007    Downs

FOREIGN PATENT DOCUMENTS

| EP | 0199535 | 10/1986 |
|---|---|---|
| EP | 0577903 | 12/1994 |
| EP | 0768375 | 4/1997 |
| EP | 1034787 | 9/2000 |
| WO | 9700078 | 1/1997 |
| WO | 9735596 | 10/1997 |
| WO | 0053200 | 9/2000 |
| WO | 0153201 | 7/2001 |
| WO | 2004112507 | 12/2004 |
| WO | 2006108824 | 10/2006 |

OTHER PUBLICATIONS

Elmer, Probiotics: "Living Drugs," Am J Health Syst Pharm, vol. 58, Jun. 15, 2001, pp. 1101-1109—XP008008536.
Vanderhoof et al., "Use of Probiotics in Childhood Gastrointestinal Disorders," Journal of Pediatric Gastroenterology and Nutrition, vol. 27, No. 3, Sep. 1998, pp. 323-332—XP009055964.
Rivero et al., "Effect of a New Infant Formula Enriched with Prebiotics, Probiotics, Nucleotides and LC-PUFA on Recovery After Infection," Advances in Experimental Medicine and Biology, vol. 569, (2005), 4 pages including pp. 186-187—XP009088018.
Salminen et al., "Probiotics: how should they be defined?" Trends in Food Science & Technology, vol. 10, (1999), pp. 107-110.
International Search Report dated Jun. 3, 2008, 3 pages.
Written Opinion of the International Searching Authority dated Jun. 3, 2008, 6 pages.

*Primary Examiner* — Debbie K Ware
(74) *Attorney, Agent, or Firm* — K&L Gates LLP

(57) ABSTRACT

The use of a probiotic *Lactobacillus rhamnosus* and a probiotic *Bifidobacterium longum* in the manufacture of a medicament or therapeutic nutritional composition for administration to an infant during at least the first three months of life for the long-term prophylaxis of diarrhea in infants and young children.

8 Claims, No Drawings

REDUCTION OF RISK DIARRHOEA

CROSS REFERENCE TO RELATED APPLICATIONS

The present application is a National Stage of International Application No. PCT/EP2008/052029, filed on Feb. 20, 2008, which claims priority to European Patent Application No. 07105078.5, filed on Mar. 28, 2007, the entire contents of which are being incorporated herein by reference.

FIELD OF THE INVENTION

This invention relates to the use of probiotic bacteria to reduce the risk of diarrhoea in infants and young children.

BACKGROUND TO THE INVENTION

Immediately before birth, the gastro-intestinal tract of a baby is thought to be sterile. During the normal process of birth, it encounters bacteria from the digestive tract, skin and environment of the mother and starts to become colonised. The faecal microbiota of healthy breast-fed infants which may be taken as the optimum microbiota for this age group is dominated by Bifidobacteria species with some Lactobacillus species and lesser amounts of Bacteroides such as Bacteriodes fragilis species, to the exclusion of potential pathogens such as Clostridia. After the completion of weaning at about 2 years of age, a pattern of gut microbiota that resembles the adult pattern becomes established.

It should be noted that, in the healthy breast-fed infant, Bifidobacteria form the basis of the microbiota accounting for 60-90% of total bacteria in the infant gut. Breast feeding also promotes intestinal barrier development which, together with bifidobacterial domination leads to enhanced absorption and therefore utilisation of ingested nutrition.

Mother's milk is recommended for all infants. However, in some cases breast feeding is inadequate or unsuccessful for medical reasons or the mother chooses not to breast feed. Infant formulae have been developed for these situations.

In the recent past, certain strains of bacteria have attracted considerable attention because they have been found to exhibit valuable properties for man if ingested. In particular, specific strains of the genera Lactobacilli and Bifidobacteria have been found to be able to colonise the intestinal mucosa, to reduce the capability of pathogenic bacteria to adhere to the intestinal epithelium, to have immunomodulatory effects and to assist in the maintenance of well-being. Such bacteria are sometimes called probiotics and it has already been proposed to add suitable probiotic bacteria to infant formulae.

Extensive studies have been carried out to identify new probiotic strains. For example, EP 0 199 535, EP 0 768 375, WO 97/00078, EP 0 577 903 and WO 00/53200 disclose specific strains of Lactobacilli and Bifidobacteria and their beneficial effects.

As indicated above, by reason of their abilities to colonise the intestinal mucosa and reduce the capacity of pathogenic bacteria to adhere to the intestinal epithelium, certain probiotic strains have already been proposed for the prevention and treatment of diarrhoea in infants. For example, WO 01/53201 proposes the use of Lactobacillus strains such as Lactobacillus paracasei CNCM I-2116 for the prevention or treatment of diarrhoea, specifically rotavirus-induced diarrhoea. A study is described in which the strain was administered to young children over a period of 29 days and it was found that the group of subjects receiving the strain had a 30% lower level of occurrence of episodes of diarrhoea during the study period.

However, incidence of episodes of infectious diarrhoea during the first few years remains a major concern for both parents and other care-givers and healthcare professionals.

SUMMARY OF THE INVENTION

During a study primarily designed to investigate the effect on growth, tolerance, and morbidity of 3 infant formulas containing different combinations of probiotic bacteria, the present inventors have surprisingly found that feeding a specific combination of probiotic bacteria during the first three to four months of life reduced the incidence of diarrhoea not only during the period in which the probiotic bacteria were administered but also for at least 8 months after administration of the probiotic bacteria had stopped.

The present invention therefore provides the use of a probiotic Lactobacillus rhamnosus and a probiotic Bifidobacterium longum in the manufacture of a medicament or therapeutic nutritional composition for administration to an infant during at least the first three months of life for the long-term prophylaxis of diarrhoea.

The invention extends to a method for the long-term prophylaxis of diarrhoea in infants and young children by administering to an infant in need thereof a therapeutic amount of a probiotic Lactobacillus rhamnosus and a probiotic Bifidobacterium longum during at least the first three months of life.

It will be appreciated that the long-term prophylaxis of diarrhoea during this important period for the development of infants and young children may have long-term benefits for the health of the subject over and above the discomfort and inconvenience associated with the episodes of diarrhoea themselves.

DETAILED DESCRIPTION OF THE INVENTION

In this specification, the following terms have the following meanings:—

"infant" means a child under the age of 6 months;

"long term prophylaxis of diarrhoea" means reduction of episodes of diarrhoea for at least eight months after administration of probiotic has ceased;

"probiotic" means microbial cell preparations or components of microbial cells with a beneficial effect on the health or well-being of the host. (Salminen S, Ouwehand A. Benno Y. et al "Probiotics: how should they be defined" Trends Food Sci. Technol. 1999: 10 107-10);

"young child" means a child between the ages of 6 and 36 months.

All references to percentages are percentages by weight unless otherwise stated.

The probiotic Lactobacillus rhamnosus may be any species of Lactobacillus rhamnosus with established probiotic characteristics. Preferred species include Lactobacillus rhamnosus ATCC 53103 obtainable inter alia from Valio Oy of Finland under the trade mark LGG and Lactobacillus rhamnosus CGMCC 1.3724.

The probiotic Bifidobacterium longum may be any species of Bifidobacterium longum with established probiotic characteristics. A preferred species is Bifidobacterium longum ATCC BAA-999 obtainable from Morinaga Milk Industry Co. Ltd. of Japan under the trade mark BB536.

A suitable daily dose of the probiotic bacteria is from 10e5 to 10e11 colony forming units (cfu), more preferably from 10e7 to 10e10 cfu.

The probiotic *Lactobacillus rhamnosus* and *Bifidobacterium longum* are preferably administered to the infant for at least the first three months of life, more preferably for the first four to six months of the life of the infant.

The probiotic bacteria may be administered directly to the infant or, if the mother is breast-feeding, via the mother. If the probiotic bacteria are to be administered via the mother, they may be supplied to the mother as a supplement in the form of tablets, capsules, pastilles, chewing gum or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. The supplement may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. In all cases, such further components will be selected having regard to their suitability for the intended recipient.

Alternatively, the probiotic bacteria may be administered to the mother in the form of a therapeutic nutritional composition. The composition may be a nutritionally complete formula.

A nutritionally complete formula for administration to pregnant women according to the invention may comprise a source of protein. Any suitable dietary protein may be used for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred. The composition may also contain a source of carbohydrates and a source of fat.

If the formula includes a fat source in addition to the DHA, the fat source preferably provides 5% to 40% of the energy of the formula; for example 20% to 30% of the energy. A suitable fat profile may be obtained using a blend of canola oil, corn oil and high-oleic acid sunflower oil.

A source of carbohydrate may be added to the formula. It preferably provides 40% to 80% of the energy of the formula. Any suitable carbohydrate may be used, for example sucrose, lactose, glucose, fructose, corn syrup solids, maltodextrins, and mixtures thereof. Dietary fibre may also be added if desired. Dietary fibre passes through the small intestine undigested by enzymes and functions as a natural bulking agent and laxative. Dietary fibre may be soluble or insoluble and in general a blend of the two types is preferred. Suitable sources of dietary fibre include soy, pea, oat, pectin, guar gum, gum Arabic, fructooligosaccharides, galacto-oligosaccharides, sialyl-lactose and oligosaccharides derived from animal milks. A preferred fibre blend is a mixture of inulin with shorter chain fructo-oligosaccharides. Preferably, if fibre is present, the fibre content is between 2 and 40 g/l of the formula as consumed, more preferably between 4 and 10 g/l.

The formula may also contain minerals and micronutrients such as trace elements and vitamins in accordance with the recommendations of Government bodies such as the USRDA. For example, the formula may contain per daily dose one or more of the following micronutrients in the ranges given: —300 to 500 mg calcium, 50 to 100 mg magnesium, 150 to 250 mg phosphorus, 5 to 20 mg iron, 1 to 7 mg zinc, 0.1 to 0.3 mg copper, 50 to 200 µg iodine, 5 to 15 µg selenium, 1000 to 3000 µg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 µg Vitamin B12, 100 to 800 µg folic acid, 30 to 70 µg biotin, 1 to 5 µg Vitamin D, 3 to 10 IU Vitamin E.

One or more food grade emulsifiers may be incorporated into the formula if desired; for example diacetyl tartaric acid esters of mono- and di-glycerides, lecithin and mono- and di-glycerides. Similarly suitable salts and stabilisers may be included.

The formula is preferably enterally administrable; for example in the form of a powder for re-constitution with milk or water.

Alternatively, or in the case of infants who are not breast fed, the probiotic may be administered as a supplement, for example as a daily dose of 10e9 cfu dissolved in water and administered on a spoon.

For infants who are not breast fed, the probiotic bacteria may be conveniently administered in an infant formula.

An infant formula for use according to the present invention may contain a protein source in an amount of not more than 2.0 g/100 kcal, preferably 1.8 to 2.0 g/100 kcal. The type of protein is not believed to be critical to the present invention provided that the minimum requirements for essential amino acid content are met and satisfactory growth is ensured although it is preferred that over 50% by weight of the protein source is whey. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in whatever proportions are desired.

The proteins may be intact or hydrolysed or a mixture of intact and hydrolysed proteins. It may be desirable to supply partially hydrolysed proteins (degree of hydrolysis between 2 and 20%), for example for infants believed to be at risk of developing cows' milk allergy. If hydrolysed proteins are required, the hydrolysis process may be carried out as desired and as is known in the art. For example, a whey protein hydrolysate may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

The infant formula may contain a carbohydrate source. Any carbohydrate source conventionally found in infant formulae such as lactose, saccharose, maltodextrin, starch and mixtures thereof may be used although the preferred source of carbohydrates is lactose. Preferably the carbohydrate sources contribute between 35 and 65% of the total energy of the formula.

The infant formula may contain a source of lipids. The lipid source may be any lipid or fat which is suitable for use in infant formulas. Preferred fat sources include palm olein, high oleic sunflower oil and high oleic safflower oil. The essential fatty acids linoleic and α-linolenic acid may also be added as may small amounts of oils containing high quantities of preformed arachidonic acid and docosahexaenoic acid such as fish oils or microbial oils. In total, the fat content is preferably such as to contribute between 30 to 55% of the total energy of the formula. The fat source preferably has a ratio of n–6 to n–3 fatty acids of about 5:1 to about 15:1; for example about 8:1 to about 10:1.

The infant formula may also contain all vitamins and minerals understood to be essential in the daily diet and in nutritionally significant amounts. Minimum requirements have been established for certain vitamins and minerals. Examples of minerals, vitamins and other nutrients optionally present in the infant formula include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population.

If necessary, the infant formula may contain emulsifiers and stabilisers such as soy lecithin, citric acid esters of mono- and di-glycerides, and the like.

The infant formula may optionally contain other substances which may have a beneficial effect such as fibres, lactoferrin, nucleotides, nucleosides, and the like.

Both the infant formula and the nutritional formula described above may be prepared in any suitable manner. For example, they may be prepared by blending together the protein, the carbohydrate source, and the fat source in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture is then homogenised; for example in two stages.

The liquid mixture may then be thermally treated to reduce bacterial loads, by rapidly heating the liquid mixture to a temperature in the range of about 80° C. to about 150° C. for about 5 seconds to about 5 minutes, for example. This may be carried out by steam injection, autoclave or by heat exchanger; for example a plate heat exchanger.

Then, the liquid mixture may be cooled to about 60° C. to about 85° C.; for example by flash cooling. The liquid mixture may then be again homogenised; for example in two stages at about 10 MPa to about 30 MPa in the first stage and about 2 MPa to about 10 MPa in the second stage. The homogenised mixture may then be further cooled to add any heat sensitive components; such as vitamins and minerals. The pH and solids content of the homogenised mixture are conveniently adjusted at this point.

The homogenised mixture is transferred to a suitable drying apparatus such as a spray drier or freeze drier and converted to powder. The powder should have a moisture content of less than about 5% by weight.

The probiotic bacteria may be cultured according to any suitable method and prepared for addition to the nutritional or infant formula by freeze-drying or spray-drying for example. Alternatively, bacterial preparations can be bought from specialist suppliers such as Morinaga and Valio already prepared in a suitable form for addition to food products such as nutritional and infant formulas. The probiotic bacteria may be added to the formula in an amount between 10e3 and 10e12 cfu/g powder, more preferably.

The invention will now be further illustrated by reference to the following examples:—

Example 1

An example of the composition of a suitable infant formula to be used in the present invention is given below

| Nutrient | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |
| *L. rhamnosus* ATCC 53103 | $2.10^7$ cfu/g of powder, live bacteria | |
| *B. longum* ATCC BAA-999 | $2.10^7$ cfu/g of powder, live bacteria | |

Example 2

284 healthy newborn infants aged up to 14 days whose mothers had elected not to breast feed were enrolled from a total of five study sites in France and randomised to one of four study groups in a prospective double blind study.

The first group consisted of 70 infants who received an infant formula (commercially available Nestlé NAN® starter formula) containing 2.10e7 cfu/g *Lactobacillus rhamnosus* ATCC 53103 and 2.10e7 cfu/g *Bifidobacterium longum* ATCC BA-999).

The second group consisted of 70 infants who received the same infant formula with the same probiotics and a mixture of prebiotic fibres (10% short chain fructo-oligosaccharides, 90% galactooligosaccharides) at 4 grams per litre of made-up formula.

The third group consisted of 74 infants who received the same infant formula with the same prebiotic fibres and 2.10e7 cfu/g *Lactobacillus casei* CNCM I-2116 and 2.10e7 cfu/g *Bifidobacterium longum* ATCC BA-999) probiotics.

The fourth group (control group) received only the unsupplemented infant formula.

All groups were fed exclusively with their assigned formula until the age of 16 weeks. The weight at age 16 weeks was recorded as were recumbent length and head circumference. A diary was kept for each infant to record stool production, flatulence, spitting and vomiting, frequency and duration of colic, frequency of episodes of morbidity (number of visits to health care professionals, other illness). The subjects were followed up to 12 months of age. It was found that the infants in the first group had had a statistically lower one year incidence of diarrhoea than the infants in groups two to four (OR=0.22, 95% CI=[0.07, 0.69], p=0.027), especially during the period from 4 to 12 months of age.

The invention claimed is:

1. A method for reducing the risk of diarrhea in an infant comprising the steps of administering to an infant during at least the first three months of life for the long-term prophylaxis of diarrhea, a composition comprising a therapeutically effective amount of a probiotic *Lactobacillus rhamnosus* and a probiotic *Bifidobacterium longum*, wherein the composition is administered to the infant via the breast-feeding mother.

2. The method of claim 1, wherein the probiotic *Lactobacillus rhamnosus* is selected from the group consisting of *Lactobacillus rhamnosus* ATCC 53103 and *Lactobacillus rhamnosus* CGMCC 1.3724.

3. The method of claim 1, wherein the probiotic *Bifidobacterium longum* is *Bifidobacterium longum* ATCC BAA-999.

4. The method of claim 1, wherein the composition is administered to the infant for the first 4 to 6 months of life.

5. The method of claim 1, wherein the composition comprises a total of between 10e5 and 10e11 cfu of probiotic bacteria per daily dose.

6. The method of claim 1, wherein the composition comprises a total of between 10e3 and 10e12 cfu of probiotic bacteria per gram of composition (dry weight).

7. The method of claim 1, wherein the composition is a therapeutic nutritional composition.

8. The method of claim 1, wherein the composition is a medicament.

* * * * *